United States Patent
Edney et al.

(10) Patent No.: US 6,803,464 B2
(45) Date of Patent: Oct. 12, 2004

(54) PROCESS FOR THE PREPARATION OF PYRAZINE COMPOUNDS

(75) Inventors: Dean David Edney, Dartford (GB); Andrew Kennedy, Dartford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 71 days.

(21) Appl. No.: 10/275,457

(22) PCT Filed: May 2, 2001

(86) PCT No.: PCT/GB01/01929

§ 371 (c)(1),
(2), (4) Date: Nov. 5, 2002

(87) PCT Pub. No.: WO01/85674

PCT Pub. Date: Nov. 15, 2001

(65) Prior Publication Data

US 2003/0149053 A1 Aug. 7, 2003

(30) Foreign Application Priority Data

May 5, 2000 (GB) .............................. 0010971

(51) Int. Cl.$^7$ ...................... C07D 241/00; C07C 257/00
(52) U.S. Cl. ........................................ 544/336; 564/246
(58) Field of Search ........................... 544/336; 564/246

(56) References Cited

FOREIGN PATENT DOCUMENTS

| WO | 98/38174 | 9/1998 |
|---|---|---|
| WO | 00/12488 | 3/2000 |

OTHER PUBLICATIONS

Lakhan, R. et al., "Novel Synthesis of Heterocycles from Chi–oxonitriles; Part III. 2–Amino–3–Arylpyrazines," *Sythesis*, DE, Gerog Thieme Verlag, Stutgart, vol. 10. pp. 914–915 (Oct. 1, 1987).

*Primary Examiner*—Richard L. Raymond
*Assistant Examiner*—Zachary C. Tucker
(74) *Attorney, Agent, or Firm*—Bonnie L. deppenbrock

(57) ABSTRACT

The present invention relates to a process for the preparation of both the phenyl pyrazine derivative 2,6-diamino-3-(2,3,5-trichlorophenyl)pyrazine and an intermediate in the synthesis of 2,6-diamino-3-(2,3,5-trichlorophenyl)pyrazine, 2-{[Cyano-(2,3,5-trichlorophenyl)-methyl]-amino}-acetamidine or a salt thereof.

11 Claims, No Drawings

PROCESS FOR THE PREPARATION OF PYRAZINE COMPOUNDS

This application is filed pursuant to 35 U.S.C. §371 as a United States National Phase Application of International Application No. PCT/GB01/01929 filed May 2, 2001, which claims priority from 0010971.0 filed May 5, 2000.

The present invention relates to a process for the preparation of both the phenyl pyrazine derivative 2,6-diamino-3-(2,3,5-trichlorophenyl)pyrazine and an intermediate in the synthesis of 2,6-diamino-3-(2,3,5-trichlorophenyl)pyrazine, 2-{[Cyano-(2,3,5-trichlorophenyl)-methyl]-amino}-acetamidine or a salt thereof.

International patent application no. PCT/EP98/01077, publication no. WO 98/38174, discloses a class of phenyl pyrazine derivatives including 2,6-diamino-3-(2,3,5-trichlorophenyl)pyrazine and pharmaceutically acceptable derivatives thereof, their use in treatment of certain CNS disorders and processes for their preparation. In particular, WO 98/38174 describes a process for producing 2,6-diamino-3-(2,3,5-trichlorophenyl)pyrazine which comprises the addition of potassium cyanide to a mixture of aminoacetamidine dihydrobromide and 2,3,5-trichlorobenzaldehyde in methanol to yield the intermediate 2-{[Cyano-(2,3,5-trichlorophenyl)-methyl]-amino}-acetamidine hydrobromide. The intermediate 2-{[Cyano-(2,3,5-trichlorophenyl)-methyl]-amino}-acetamidine hydrobromide is reacted with lithium hydroxide in methanol to yield 2,6-diamino-3-(2,3,5-trichlorophenyl) pyrazine.

The process described in WO 98/38174 has a number of disadvantages. Specifically, the reaction is characterised by poor yields, a problem which is exacerbated by the fact that the 2-{[Cyano-(2,3,5-trichlorophenyl)-methyl]-amino}-acetamidine hydrobromide is unstable to the basic conditions which exist towards the end of the reaction.

We have now surprisingly found that by careful control of the reaction conditions and by judicious choice of the order of addition of the reactants the above mentioned disadvantages may be alleviated. In particular, we have found that by mixing a cyanide source with an acid salt of aminoacetamidine before addition of 2,3,5-trichlorobenzaldehyde to the reaction mixture the yield of the reaction is increased.

Accordingly, the present invention provides a process for the preparation of 2-{[Cyano-(2,3,5-trichlorophenyl)-methyl]-amino}-acetamide or a salt thereof which process comprises the steps of:

(i) reaction of an acid salt of aminoacetamidine with a source of cyanide; and (ii) reaction of the product of step (i) with 2,3,5-trichlorobenzaldehyde.

Without wishing to be bound by theory, it is thought that in the prior art process the acidity of the initial reaction mixture, caused by the presence of the acid associated with the aminoacetamidine, leads to irreversible formation of acetals and hemiacetals from 2,3,5-trichlorobenzaldehyde. However, in the process of the present invention it is believed that the cyanide source reacts with the acid salt of the aminoacetamidine to form an aminoacetamidine mono acid mono hydrocyanide salt thereby reducing the acidity of the solution and thus reducing the tendency of the 2,3,5-trichlorobenzaldehyde to form acetals and hemiacetals. Moreover, because the cyanide source exists as a hydrocyanide salt of aminoacetamidine the reaction mixture is less basic at the end of the reaction and consequently the 2-{[Cyano-(2,3,5-trichlorophenyl)-methyl]-amino}-acetamidine is more stable in the product mixture.

The process of the present invention leads to an increase in yield of about 35% compared with the process described in the prior art.

The reaction may be effected in any suitable solvent or mixture of solvents. Preferably the solvent is a polar solvent such as an alcohol, e.g. methanol, ethanol, isopropyl alcohol, or dimethylformamide. Methanol is most preferred.

The process may be effected at any suitable temperature. Suitably, reaction step (i) is conducted at room temperature and reaction step (ii) is conducted at elevated temperature, preferably at about 50° C.

It will be appreciated that the relative amounts of aminoacetamidine, cyanide; and 2,3,5-trichlorobenzaldehyde may be varied. Preferably the aminoacetamidine or 2,3,5-trichlorobenzaldehyde is in excess, most preferably the aminoacetamidine is in excess.

Suitable sources of cyanide include potassium cyanide, sodium cyanide, tetrabutylammonium cyanide, preferably, potassium cyanide.

It will be appreciated that any suitable acid salt of aminoacetamidine may be used in the reaction. Examples of suitable acid salts include inorganic acid salts such as hydrochloric and hydrobromic acid, and organic acid salts such as maleic and formic acid.

2,3,5-trichlorobenzaldehyde may be prepared according to the methods described in WO95/07877.

Aminoacetamidine, may be prepared according to known procedures, for example, those described in Chem. Berichte, 89, 1185 (1956).

2-{[Cyano-(2,3,5-trichlorophenyl)-methyl]-amino}-acetamidine or a salt thereof is particularly useful as an intermediate in the synthesis of 2,6-diamino-3-(2,3,5-trichlorophenyl)pyrazine.

Accordingly, in a further aspect, the present invention provides a process for the preparation of 2,6-diamino-3-(2,3,5-trichlorophenyl)pyrazine or a pharmaceutically acceptable derivative thereof which process. comprises the steps of:

(i) reaction of an acid addition salt of aminoacetamidine with a source of cyanide;

(ii) reaction of the product of step (i) with 2,3,5-trichlorobenzaldehyde to afford 2-{[Cyano-(2,3,5-trichlorophenyl)-methyl]-amino}-acetamidine or a salt thereof; and (iii) cyclisation and oxidation of 2-{[Cyano-(2,3,5-trichlorophenyl)-methyl]-amino}-acetamidine or a salt thereof.

Suitable conditions for the cyclisation and oxidation of 2-{[Cyano-(2,3,5-trichlorophenyl)-methyl]-amino}-acetamidine or a salt thereof (step(iii)) are well known in the literature. For example the reaction may be effected by neutralising a salt of a compound of 2-{[Cyano-(2,3,5-trichlorophenyl)-methyl]-amino}-acetamidine, e.g. with lithium hydroxide in a suitable solvent such as an alcohol, e.g. methanol, under which conditions spontaneous oxidation to 2,6-diamino-3-(2,3,5-trichlorophenyl)pyrazine occurs.

By pharmaceutically acceptable derivative is meant any pharmaceutically acceptable salt or solvate of 2,6-diamino-3-(2,3,5-trichlorophenyl)pyrazine, or any other compound which upon administration to the recipient is capable of providing (directly or indirectly) 2,6-diamino-3-(2,3,5-trichlorophenyl)pyrazine or an active metabolite or residue thereof (e.g. a prodrug). Suitable prodrugs are well-known in the art and include N-acyl derivatives, for example at any of the nitrogen atoms in 2,6-diamino-3-(2,3,5-trichlorophenyl)pyrazine, for example simple acyl derivatives such as acetyl, propionyl and the like or groups such as R—O—CH$_2$-nitrogen or R—O—C(O)-nitrogen.

EXPERIMENTAL

| HPLC METHOD | |
|---|---|
| Analytical Column | PRODIGY ODS(3), 15 cm × 4.6 mm i.d. packed with 3 μm packing |
| Mobile Phase A | Water/acetonitrile/methanol/formic acid 700/150/150/0.5 |
| Mobile Phase B | Water/acetonitrile/methanol/formic acid 200/750/50/0.5 |

| Gradient | [Time (mm)] | [Component A (%)] | [Component B(%)] |
|---|---|---|---|
| | 0 | 90 | 10 |
| | 30 | 10 | 90 |
| | 40 | 10 | 90 |
| | 41 | 90 | 10 |
| | 50 | 90 | 10 |

| | |
|---|---|
| Flow Rate | 1 ml per minute |
| Temperature | 20° C. |
| UV detection wavelength | 225 nm |
| Column Loading Typical Injection Volume | 1.25 μg |
| | 5 μL |
| Approximate Run Time | 50 minutes |

2-{[Cyano-(2,3,5-trichlorophenyl)-methyl]-amino}-acetamidine

Potassium cyanide (6.1 Kg) was dissolved in methanol (119 Kg) at 50° C. over 1 hour. Aminoacetamidine dihydrobromide (19.6 Kg) was added to the potassium cyanide solution in one portion and stirred at 25° C. for 15 minutes to allow formation of the mono acid mono hydrocyanide salt. Subsequently, 2,3,5-trichlorobenzaldehyde (24.2 Kg) was added to the reaction mixture in one portion and the mixture was stirred at 50° C. for 16 hours. On cooling to 25° C., vacuum was applied and the mixture concentrated to 5 volumes. Isopropyl ether (145 Kg) was added over 30 minutes and the mixture stirred at 20° C. overnight. The crude product was isolated by filtration and the cake washed with isopropyl ether (43 Kg). The crude product was slurried with ethyl acetate (158 kg). and water (100 kg) overnight at 20° C. The product was isolated by filtration washed with water (50 Kg), ethyl acetate (90 Kg) and vacuum dried at 400C to afford 2-{[Cyano-(2,3,5-trichlorophenyl)-methyl]-amino}-acetamidine hydrobromide. Yield 17.43 Kg (50% -92% w/w assay). HPLC retention time 3.9 minutes.

2,6-Diamino-3-(2,3,5-trichlorophenyl) pyrazine

Lithium hydroxide monohydrate (2.9 kg) was stirred in methanol (269 kg) for 60 minutes at 20° C. and then cooled to −10C. 2-{[Cyano-(2,3,5-trichlorophenyl)-methyl]-amino}-acetamidine hydrobromide was added in one portion and the resultant mixture stirred vigorously with cooling at −10° C. Compressed air was gassed over the surface of the reaction for at least 6 hours. The mixture was warmed to 25° C. and concentrated to 3 volumes under vacuum. Water (289 kg) was added over at least 1 hour with stirring. The product was isolated by filtration and the cake washed with water (51 kg) and dried in vacuo at 40° C. Yield 12 Kg (91%). HPLC retention time 11.9 minutes.

Throughout the specification and the claims which follow, unless the context requires otherwise, the word "comprise", and variations such as "comprises" and "comprising", will be understood to imply the inclusion of a stated integer or step or group of integers but not to the exclusion of any other integer or step or group of integers.

The application of which this description and claims forms part, may be used as a basis for priority in respect of any subsequent application. The claims of such subsequent application may be directed to any feature or combination of features described herein. They may take the form of product, composition, process or use claims and may include, by way of example and without limitation, one or more of the following claims:

What is claimed is:

1. A process for the preparation of 2-{[Cyano-(2,3,5-trichlorophenyl)-methyl]-amino}-acetamidine or a salt thereof which process comprises the steps of:

(i) reaction of an acid salt of aminoacetamidine with a source of cyanide; and (ii) reaction of the product of step (i) with 2,3,5-trichlorobenzaldehyde.

2. The process as claimed in claim 1 wherein the process is effected in a solvent or mixture of solvents.

3. The process as claimed in claim 1 wherein the reaction step (i) is conducted at room temperature.

4. The process as claimed in claim 1 wherein the reaction step (ii) is conducted at an elevated temperature of about 50° C.

5. The process as claimed in claim 1 wherein the aminoacetamidine is in excess.

6. The process as claimed in claim 1 wherein the source of cyanide is selected from potassium cyanide, sodium cyanide, and tetrabutylammonium cyanide.

7. The process for the preparation of 2,6-diamino-3-(2,3,5-trichlorophenyl)pyrazine or a pharmaceutically acceptable salt thereof which comprises carrying out the process of claim 1 and further comprises cyclisation and oxidation of 2-{[Cyano-(2,3,5-trichlorophenyl)-methyl]-amino}-acetamidine or a salt thereof.

8. The process of claim 1 wherein a polar solvent is employed; step (I) is conducted at room temperature; step (II) is conducted at an elevated temperature of about 50° C.; the aminoacetamide is in excess.

9. The process of claim 8 wherein the source of cyanide is selected from potassium cyanide, sodium cyanide, and tetrabutylammonium cyanide.

10. The process for the preparation of 2,6-diamino-3-(2,3,5-trichlorophenyl)pyrazine or a pharmaceutically acceptable salt thereof which comprises carrying out the process of claim 9 and further comprises cyclisation and oxidation of 2-{[Cyano-(2,3,5-trichlorophenyl)-methyl]-amino}-acetamidine or a salt thereof.

11. The process as claimed in claim 2 wherein a polar solvent is employed.

* * * * *